(12) United States Patent
Roop (10) Patent No.: US 9,176,076 B2
(45) Date of Patent: Nov. 3, 2015

(54) CARGO INSPECTION SYSTEM

(75) Inventor: Stephen S. Roop, College Station, TX (US)

(73) Assignee: The Texas A&M University System, College Station, TX (US)

( * ) Notice: Subject to any disclaimer, the term of this patent is extended or adjusted under 35 U.S.C. 154(b) by 905 days.

(21) Appl. No.: 13/405,690

(22) Filed: Feb. 27, 2012

(65) Prior Publication Data
US 2012/0219389 A1 Aug. 30, 2012

Related U.S. Application Data

(60) Provisional application No. 61/447,553, filed on Feb. 28, 2011.

(51) Int. Cl.
*G01N 23/00* (2006.01)
*G01V 5/00* (2006.01)
(Continued)

(52) U.S. Cl.
CPC .............. *G01N 23/00* (2013.01); *G01V 5/0008* (2013.01); *B61B 13/04* (2013.01); *B65G 47/74* (2013.01)

(58) Field of Classification Search
CPC ... G01N 5/0016; G01N 5/0008; G01N 5/005; G01N 23/04; G01N 23/046; G01N 23/00; G01N 2223/639; G01N 2223/419; G01N 2223/629; G01N 2223/66; G01N 2291/02881; G01N 2291/044; G01N 23/02; G01N 23/207; G01N 29/024; G01N 29/0609; G01N 29/07; G01N 29/222; G01N 29/223; G01N 29/32; G01V 5/0008; G01V 5/0075; G01V 5/0091; G01V 5/005; G09B 15/08; G01T 3/00

USPC ..................................................... 378/57, 62
See application file for complete search history.

(56) References Cited

U.S. PATENT DOCUMENTS 6,370,222 B1 4/2002 Cornick, Jr. .................... 378/57
2002/0176531 A1* 11/2002 McClelland et al. ........... 378/57
(Continued)

FOREIGN PATENT DOCUMENTS

CN 200996943 12/2007
CN 101606084 12/2009

OTHER PUBLICATIONS

Australian Government, IP Australia, Patent Application No. 2012259385, Patent Examination Report No. 1, 3 pages, Dec. 19, 2014.

(Continued)

*Primary Examiner* — Irakli Kiknadze
(74) *Attorney, Agent, or Firm* — Baker Botts L.L.P.

(57) ABSTRACT

According to one embodiment, a cargo inspection method includes transporting a first guideway vehicle over a guideway from a first inspection station to a second inspection station. A first non-intrusive scanning mechanism associated with the first inspection station is used to acquire a first set of data associated with cargo stored in the first guideway vehicle. The first set of data acquired by the first non-intrusive scanning mechanism associated with the first inspection station is analyzed to determine the identity of the cargo stored on the first guideway vehicle. The first set of data acquired by the first non-intrusive scanning mechanism is compared with a first manifest that describes the cargo that is declared to be stored on the first guideway vehicle. It is determined that the first guideway vehicle contains contraband cargo if the identity of the cargo does not match the first manifest.

23 Claims, 3 Drawing Sheets

(51) Int. Cl.
    *B61B 13/04*  (2006.01)
    *B65G 47/74*  (2006.01)

(56) References Cited

U.S. PATENT DOCUMENTS

| | | | |
|---|---|---|---|
| 2002/0186862 A1 | 12/2002 | McClelland | |
| 2006/0203962 A1 | 9/2006 | Hu et al. | 378/57 |
| 2007/0165777 A1 | 7/2007 | Anwar et al. | 378/57 |
| 2008/0042842 A1* | 2/2008 | Ulibarri | 340/572.1 |
| 2008/0198967 A1* | 8/2008 | Connelly et al. | 378/57 |

OTHER PUBLICATIONS

Mexican Institute of Industrial Property, First Office Action and English translation re: Communication of results regarding substantive examination, Mexican Patent Application No. MX/a/2013/009884, received from foreign associate Jan. 5, 2015, 6 total pages.
PCT, Notification of Transmittal of the International Search Report and the Written Opinion of the International Searching Authority, or the Declaration, International Application No. PCT/US2012/026842, 9 pages, Oct. 5, 2012.
State Intellectual Property Office of the People's Republic of China, Application No. 201280010807.2, The First Office Action with Search Report (PCT application in Chinese national phase) with English translation, dated Sep. 1, 2015.
Divisional Direction of Patents; Divisional Sub-Direction of Substantive Examination of Patents; File: MX/a/2013/009884 of PCT Patent; Requirement 2, Subject: Notice of the Result of Substantive Examination with English Translation; Record 42487; dated May 26, 2015, forwarded by Foreign Associate to Baker Botts on Sep. 10, 2015.

* cited by examiner

CARGO INSPECTION SYSTEM

RELATED APPLICATION

This application claims benefit under 35 U.S.C. §119(e) of U.S. Provisional Application Ser. No. 61/447,553, entitled "CARGO INSPECTION SYSTEM," filed Feb. 28, 2011, by Stephen S. Roop, which is incorporated herein by reference.

TECHNICAL FIELD OF THE DISCLOSURE

This disclosure generally relates to transportation systems, and more particularly, to a cargo inspections system and a method of operating the same.

BACKGROUND OF THE DISCLOSURE

Various transport mechanisms may be used for the transport of products from producers to consumers. Examples of such mechanisms include trucks that travel over a roadway, ships that move over bodies of water, and guideway vehicles that travel over land-based guideway systems. Whereas trucks may be efficient for transporting products relatively short distances, guideway systems may be more practical for transporting large quantities of products over relatively long distances. In contrast to typical railway systems that use a pair of rails, a guideway system include a single guideway made of a structurally rigid material. Automated transport vehicles are guided over the guideway along a predetermined path.

Regardless of the mechanism used, various difficulties, such as theft and/or inclusion of contraband materials, may be encountered during the shipment of products from one location to another. Previous solutions to the problems include the inspection of the products and/or containers before and after shipment. However, inspection is relatively difficult to implement where large quantities of products are transported and/or where multiple transport mechanisms have been used. This may be particularly true where the transport of the goods is across international borders.

SUMMARY OF THE DISCLOSURE

According to one embodiment, a cargo inspection method includes transporting a first guideway vehicle over a guideway from a first inspection station to a second inspection station. A first non-intrusive scanning mechanism associated with the first inspection station is used to acquire a first set of data associated with cargo stored in the first guideway vehicle. The first set of data acquired by the first non-intrusive scanning mechanism associated with the first inspection station is analyzed to determine the identity of the cargo stored on the first guideway vehicle. The first set of data acquired by the first non-intrusive scanning mechanism is compared with a first manifest that describes the cargo that is declared to be stored on the first guideway vehicle. It is determined that the first guideway vehicle contains contraband cargo if the identity of the cargo does not match the first manifest.

Some embodiments of the disclosure may provide numerous technical advantages. For example, one embodiment of the cargo inspection system may use the non-stop transport of guideway vehicles between first and second inspection stations. Eliminating stopping points, in this manner, may improve the integrity of the cargo since stopping points provide an opportunity for the removal and/or addition of cargo to the guideway vehicles. The velocity of the guideway vehicles at speeds up to 100 kph may also improve the security of the cargo that is being transported. Additionally, in certain embodiments, the system may include the non-stop movement of the guideway vehicles through the first and second inspection stations. Such non-stop movement may provide sufficient throughput to provide up to 100 percent inspection of cargo moving through the cargo inspection system in certain embodiments.

In certain embodiments, the cargo inspection system may be operated in accordance with governmental trade policies and procedures. For example, the cargo inspection system may be developed in accordance with Customs-Trade Partnership Against Terrorism (C-TPAT) policies and procedures. Because cargo can be inspected at remotely separated locations and while the guideway vehicles are in motion, the cargo inspection system may have the advantage of moving the inspection process away from congested border locations. Additionally, the cargo inspection system may automate many of the activities previously performed manually by customs personnel.

Still another advantage may be that the cargo inspection system encourages communication between governmental entities. For example, in particular embodiments, information obtained at one inspection station associated with a governmental entity may be forwarded, in real time, to customs officers associated with a bordering governmental entity. Another advantage may be that data flow between government entities is symmetrical so that reciprocity concerns from foreign nations are eliminated or reduced. As such, the cargo inspection system may eliminate the problems associated with monitoring foreign custom practices and data availability.

Some embodiments may benefit from some, none, or all of these advantages. Other technical advantages may be readily ascertained by one of ordinary skill in the art.

BRIEF DESCRIPTION OF THE DRAWINGS

A more complete understanding of embodiments of the disclosure will be apparent from the detailed description taken in conjunction with the accompanying drawings in which.

DETAILED DESCRIPTION OF EXAMPLE EMBODIMENTS

Products may be shipped from one location to another using a variety of different transport mechanisms. However, various difficulties may be encountered during transportation. For example, products may be stolen from the shipping containers prior to the products being received at their destination. Conversely, contraband or other unauthorized materials may be slipped into the shipping containers prior to the products being received at their destination.

Previous approaches for mitigating these difficulties have included the inspection of cargo before and/or after shipment. However, where large quantities of products are being transported, inspection may be difficult to implement. For example, a country may export and/or import large quantities of products to and/or from other countries. Due to the large quantity of the products being transported, it may take a relatively long time to fully inspect each item or cargo shipment. As a result, only a portion of a shipment being transported across a geographic boundary may be typically inspected. Some shipments may evade inspection altogether. As a result, certain shipments crossing into or out of the country or otherwise being transported across a geographic boundary may remain susceptible to tampering.

The Department of Homeland Security (DHS) and its agency, the Customs and Border Protection (CBP), are the focal point of the United State's efforts to secure trade. Domestic security has become a major consideration for the United States when importing of goods and materials from international trading partners. The integrity of the cargo is particularly important to the United States. In particular, the threat of biological, chemical, or nuclear agents being unknowingly imported continues to be a significant concern to the government and commercial sectors.

Figure 1:
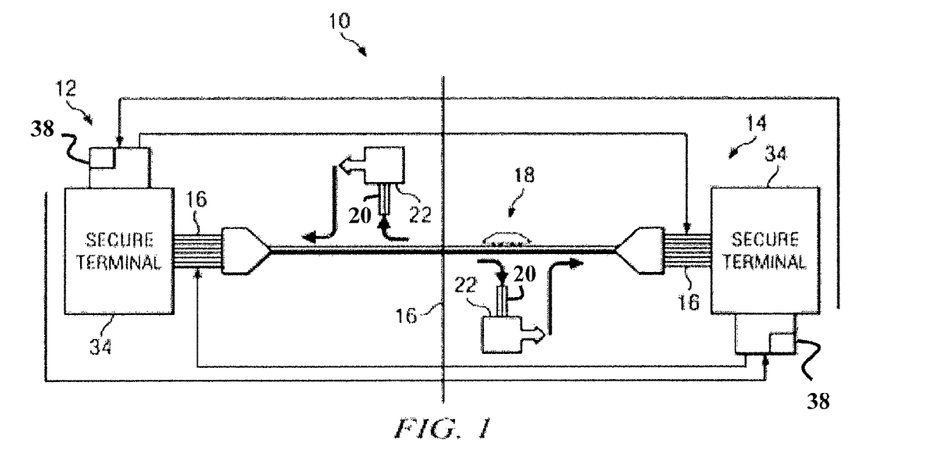
FIG. 1 illustrates a cargo inspection system, according to certain embodiments of the present disclosure.

FIG. 1 illustrates a cargo inspection system 10 according to certain embodiments of the present disclosure. Cargo inspection system 10 includes a first inspection station and a second inspection station 14. In the illustrated embodiment, first and second inspection stations 12 and 14 are located remotely from one another and are separated by a geographic boundary 16. First inspection station 12 and second inspection station 14 each have one or more non-intrusive scanning mechanisms 20 and a manual inspection depot 22. In a particular embodiment, first inspection station 12 and second inspection station 14 administer the passage of vehicles via a guideway system 18 that extends from first inspection station 12 to second inspection station 14.

Figure 2A:
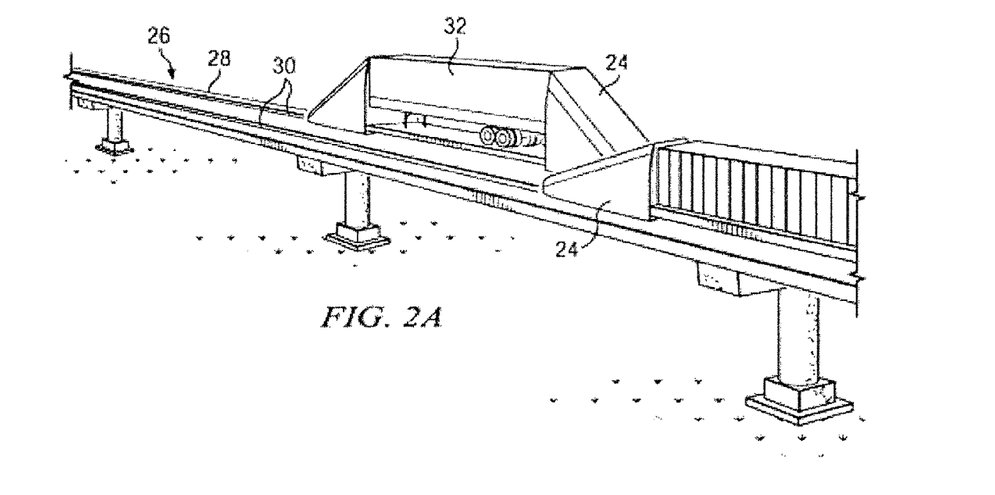
FIGS. 2A and 2B illustrate several guideway vehicles travelling over an example guideway, according to certain embodiments of the present invention.
Figure 2B:
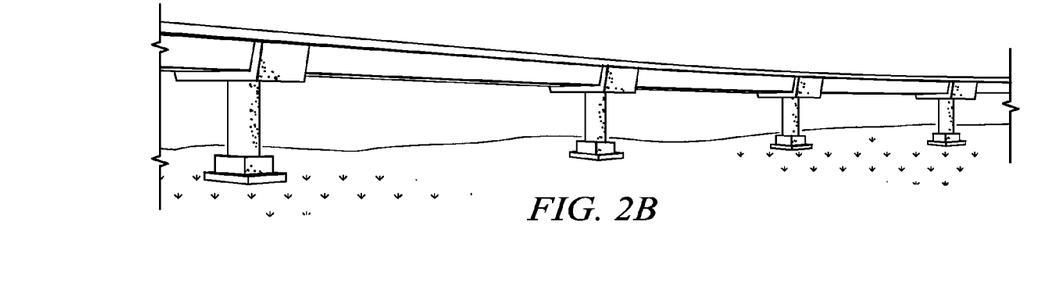

FIGS. 2A and 2B are illustrations of an example guideway system 18 that may utilize the cargo inspection system 10 of FIG. 1. A guideway system 18 includes any type of transportation system in which automated guideway vehicles 24 are guided along predetermined paths using a guideway 26. Guideway vehicles 24 are best characterized as driverless electric trucks that are engineered to operated as autonomous-units. Guideway vehicles 24 operate as single units with single loads like over-the road trucks. The guideway vehicles 24 may be operated at speeds up to approximately 100 kph and are designed to accommodate either containers or semi-trailers.

While a typical railway system uses a pair of elongated steel rails that are spaced apart a specified distance from one another and configured to guide its associated transport vehicles using flange-shaped wheels, guideway system 18 utilizes a single elongated guideway 26 for guidance of its associated guideway vehicles 24. Guideway 26 has a generally flat running surface 28 for supporting the wheels of guideway vehicles 24, and a single elongated guideway rail 30 centrally configured on the flat running surface 28. The single guideway rail 30 is typically made of a structurally rigid material that controls lateral movement of guideway vehicles 24 on the flat running surface 28. In a particular embodiment, for example, guideway 26 may be formed of metal and/or concrete.

Guideway system 18 incorporating a single elongated guideway rail 30 may provide certain advantages over known railway systems that have multiple rails. For example, guideway vehicles 24 may not be as susceptible derailment problems caused by mis-alignment of the rails of railway systems using multiple rails. Thus, guideway systems may experience enhanced reliability and/or reduced maintenance relative to known railway systems having multiple rails that support and guidance of their associated vehicles.

Guideway vehicles 24 may be any type of vehicle suitable for movement along guideway 26. Guideway vehicles 24 may include a cargo bay for storage of product as well as a motor for movement along the guideway 26. In certain embodiments, guideway vehicles may be configured with linear induction motors that operate in conjunction with the guideway rails of guideways 26 to provide a motive force for movement of guideway vehicles 24 along guideway 26. Guideway vehicles 24 may be configured with an onboard controller such that they may operate without an onboard pilot or driver.

In certain embodiments, guideway vehicles 24 may be configured with intermodal containers 32 for storage of its cargo. Intermodal container 32 may include any suitable type of container for housing product during shipment. In particular embodiments, intermodal container 32 has a structure that provides for transport over a differing type of transport system, such as a truck that travels over a roadway. In this manner, cargo stored in intermodal container 32 may be transported over guideway 26 and/or roadway without placement in another housing structure. In some cases, intermodal containers 32 may have a generally box-like shape for placement on or within a cavity of the guideway vehicle 24.

Returning to FIG. 1, first inspection station 12 and/or second inspection station 14 includes one or more non-intrusive scanning mechanisms 20 that acquires imagery of cargo stored in guideway vehicles 24 such that the identity of the stored cargo may be analyzed during transit of guideway vehicles 24 between first inspection station 12 and second inspection station 14. Non-intrusive scanning mechanisms 20 may contain any of a variety of sensor systems. For example, non-intrusive scanning mechanisms 20 may include gamma-ray, radiological, or other scanning systems for scanning guideway vehicles 24 to obtain data identifying cargo stored on the guideway vehicles 24.

First inspection station 12 and second inspection station 14 may each include a secure terminal 34. Secure terminals 34 provide a central repository for guideway vehicles 24 bound for transit across guideway 26. Each of first inspection station 12 and second inspection station 14 may include a communication system 36. Communication system 36 may cooperate to provide communication between the two respective inspection stations 12 and 14. For example, communications systems 36 may be used to transmit information between the two inspection stations 12 and 14 so that manifests and other information may be shared between the two inspection stations 12 and 14. In a particular embodiment, communications systems 36 may be used to receive and/or transmit data acquired by non-intrusive scanning mechanisms 20 at either inspection station 12 or 14 to the other inspection station 12 or second inspection station 14.

First inspection station 12 and second inspection station 14 may house personnel who may administer the operation of guideway vehicles 24 through cargo inspection system 10. Because cargo inspection system 10 may be well suited for operation across national boundaries, either or both of first inspection station 12 and second inspection station 14 may include a customs office 38 associated with a government entity. For example, where cargo inspection system 10 is located proximate a border of the United States, customs office 38 associated with first inspection station 12 may house Customs and Border Protection (CBP) personnel associated with the United States. Likewise, customs office 38 of second inspection station 14 may house customs personnel associated with a bordering country such as Mexico or Canada. In such an embodiment, first and second inspection stations 12 and 14 may function to regulate the movement of products according to national tariff agreements, and/or restrict the movement of contraband goods between the United States and Mexico or Canada.

Certain embodiments of guideway vehicles 24 may be configured to move non-stop between first inspection station 12 and second inspection station 14. That is, guideway vehicles 24 may be configured to move between first inspection station 12 and second inspection station 14 without any programmed stopping points in between. In this manner, the integrity of the cargo may be enhanced by eliminating stopping points that may provide an entry point for removal and/or addition of cargo to guideway vehicles 24. Additionally, non-stop movement through first inspection station 12 and second inspection station 14 may provide sufficient throughput to provide up to 100 percent inspection of cargo moving through cargo inspection system 10 in certain embodiments.

Certain embodiments that transport cargo using guideway vehicles 24 may be particularly useful in that the integrity of their cargo may be relatively well controlled during transit between first inspection station 12 and second inspection station 14. For example, guideway vehicles 24 may be generally relegated to movement upon guideway 22 such that they may not be easily diverted onto other types of roadways. Thus, potential illicit removal and/or addition of cargo to guideway vehicles 24 may be reduced by the inherent restricted movement provided by guideway vehicles 24 over their associated guideways 26. Also, their restricted movement may provide for automated control in which certain guideway vehicles 24 may be unmanned or void of an onboard drivers or pilots. In this manner, potential problems associated with transport systems having manned drivers or pilots who may act illicitly may be reduced or eliminated.

In operation, non-intrusive scanning mechanism 20 associated with first inspection station 12 may be used to scan guideway vehicles 24 while guideway vehicles 24 pass through or are otherwise proximate to first inspection station 12. The scan of guideway vehicles 24 may be used to generate data associated with cargo stored in guideway vehicles 24. The data may be analyzed by either of first inspection station 12 or second inspection station 14 to determine the identity of the cargo on guideway vehicle 24. In certain embodiments, the acquired data may be analyzed automatically using equipment, such as image processing equipment that generates imagery of the stored cargo. The acquired data may also be analyzed manually by personnel who determine whether cargo within in a particular guideway vehicle 24 is suspicious enough to warrant further investigation.

In particular embodiments, first inspection station and/or second inspection station 14 may generate or receive a manifest associated with guideway vehicles 24. The manifest may include a list of items that are declared to exist on the guideway vehicles 24. Either or both of first inspection station 12 and second inspection station 14 may compare the data acquired using the non-intrusive scanning mechanism 20 with the declared manifest. If the data identifying the actual cargo on a guideway vehicle 24 differs from the manifest associated with the guideway vehicle 24, the vehicle may be segregated upon arrival at manual inspection depot 22. Movement of railway vehicles from second inspection station 14 to first inspection station 12 may be conducted in a likewise manner in a reverse direction to regulate the movement of products from second inspection station 14 to first inspection station 12.

Figure 3:
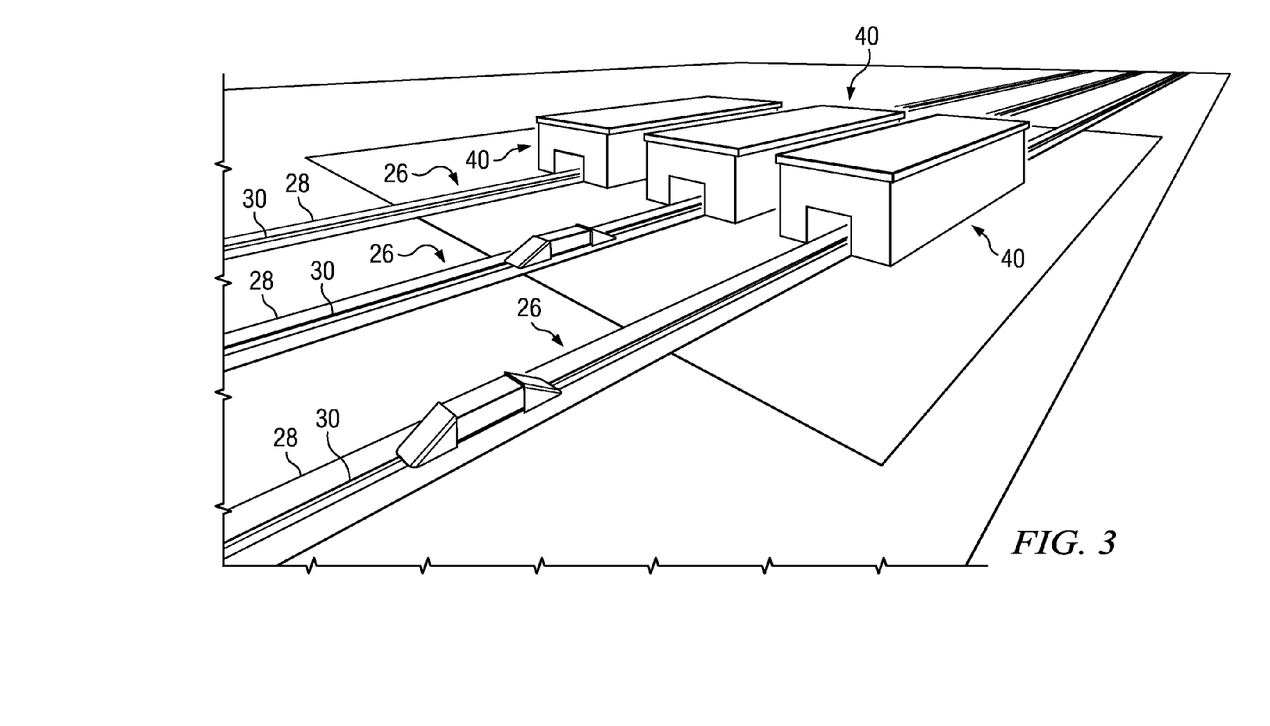
FIG. 3 illustrates multiple inspection stalls that may be configured with non-intrusive scanning mechanisms, according to certain embodiments of the present disclosure.

FIG. 3 is an illustration showing one embodiment of multiple stalls 40 that may each be configured with a non-intrusive scanning mechanism 20 (FIG. 4A or 4B) at the first inspection station 12 or second inspection station 14 of FIG. 1. Stalls 40 house non-intrusive scanning mechanisms 20 and are configured over parallel guideways 26 such that guideway vehicles 24 may pass through at least one stall without stopping as it proceeds between first inspection station 12 and second inspection station 14. In the particular embodiment shown, three non-intrusive scanning mechanisms 20 are provided for scanning guideway vehicles 24 that are to be transported between first inspection station 12 and second inspection station 14. In other embodiments, any quantity of non-intrusive scanning mechanisms 30 may be included at first inspection station 12 and/or second inspection station 14. For example, first inspection station 12 and/or second inspection station 14 may have one, two, or four or more non-intrusive scanning mechanisms 20.

Certain embodiments including multiple non-intrusive scanning mechanisms 20 may provide an advantage in that acquiring data associated with the identity of cargo in each guideway vehicle 24 may be performed while guideway vehicle 24 is moving. That is, acquisition of data associated with the cargo of each guideway vehicle 24 may be provided without stopping the guideway vehicle 24 during acquisition. In this manner, guideway vehicles 24 may proceed between first inspection station 12 and second inspection station 14 in a non-stop fashion such that potential tampering with the cargo of guideway vehicles 24 may be reduced. Multiple non-intrusive scanning mechanisms 20 may provide for increased capacity of guideway vehicles 24 than may otherwise be provided by a single non-intrusive scanning mechanism.

Figure 4A:
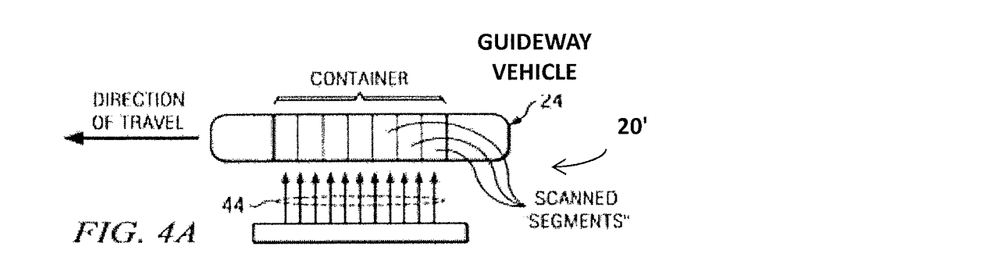
FIGS. 4A and 4B illustrate various non-intrusive scanning mechanisms that may be used by a cargo inspection system, according to certain embodiments of the present disclosure.

FIG. 4A is a diagram showing one embodiment of a serial non-intrusive scanning mechanism 20' of the cargo inspection system 10 of FIG. 1. Serial non-intrusive scanning mechanism 20' may be used to perform a serial non-intrusive scanning technique of the cargo of a guideway vehicle 24. As shown, non-intrusive scanning mechanism 20' projects energy 44 toward guideway vehicle 24 while it is moving through the non-intrusive scanning mechanism's associated stall 40, and receives reflected and/or refracted energy that may be indicative of the identity of cargo stored in guideway vehicle 24. The serial non-intrusive scanning mechanism 20 using a serial scanning technique in which energy is projected toward guideway vehicle 24 serially as guideway vehicle 24 moves through stall 40. By arranging energy 44 serially, the rate of scanning for any one guideway vehicle 24 may be increased by scanning individual "slices" of the cargo in guideway vehicle 24 and combining these as guideway vehicle 24 passes through stall 40.

Energy 44 used by serial non-intrusive scanning mechanism 20 may be any suitable type that penetrates at least partially into the cargo area of guideway vehicle for gathering data indicative of the cargo's characteristics. In certain embodiments, serial non-intrusive scanning mechanism 20 may include, but is not limited to, an X-ray machine, a gamma ray detection machine, and a computing tomography (CT) scanning machine.

Serial non-intrusive scanning mechanism 20' may generate energy 44 at relatively higher levels due to unmanned operation of guideway vehicles 24 than could otherwise be generated towards guideway vehicles 24 that have onboard occupants. Known scanning systems typically require the driver leave the vehicle while an auxiliary device tows the vehicle through the scanning mechanism; a process that may be both slow and cumbersome. Certain embodiments of guideway vehicles 24 having automated control for unmanned operation may possess an additional advantage in that they may be scanned at relatively higher energy levels for enhanced detection of cargo without potentially harming personnel who may be onboard.

Figure 4B:
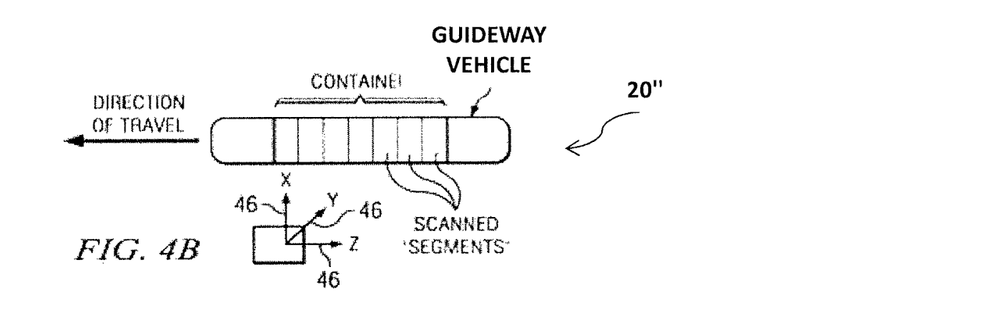
Figure 5:
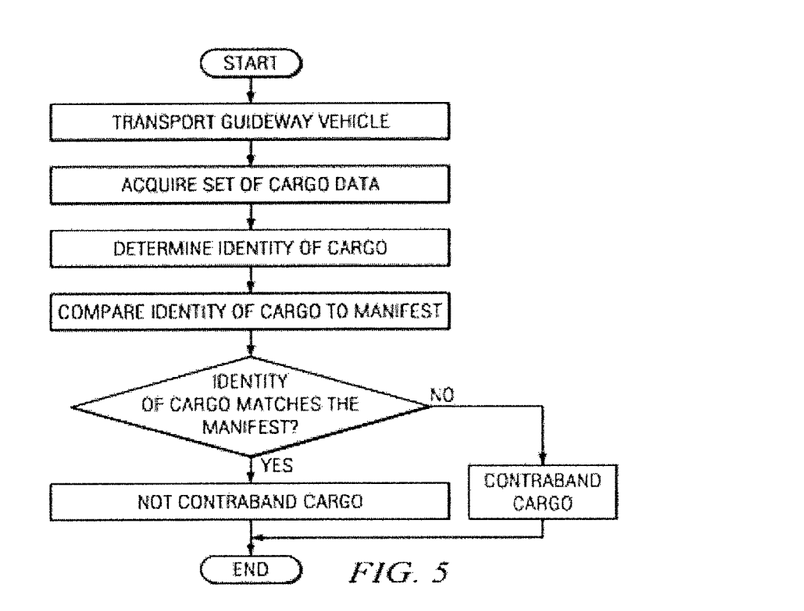

FIG. 4B is a diagram showing one embodiment of a multi-axial non-intrusive scanning mechanism 20" of the cargo inspection system 10 of FIG. 1. Multi-axial non-intrusive scanning mechanism 20" may be used to perform a multi-axial non-intrusive scanning technique. Multi-axial non-intrusive scanning mechanism 20" is similar to the serial non-intrusive scanning mechanism 20' of FIG. 3 in that it projects energy 46 toward guideway vehicle 24 while it is moving through the non-intrusive scanning mechanism's associated stall 40, and receives reflected and/or refracted energy that may be indicative of the identity of cargo stored in guideway vehicle 24. Multi-axial non-intrusive scanning mechanism 20" differs, however, in that it projects energy 46 toward guideway vehicle 24 at differing directions relative to the orientation and traveling direction of guideway vehicle 24. Certain embodiments of multi-axial non-intrusive scanning mechanism 20" may provide an advantage in that projecting energy toward the cargo area of guideway vehicle 24 may provide enhanced imagery relative to imagery generated using the serial non-intrusive scanning mechanism technique. That is, projecting energy 46 at differing directions may provide a relatively flexible analysis of cargo stored in guideway vehicles 20 by viewing and/or processing data from differing "view-points" relative to one another. Multi-axial non-intrusive scanning mechanism 20" may use similar mechanisms as those described with reference to the serial non-intrusive scanning mechanism 20' of FIG. 3. Projecting energy Modifications, additions, or omissions may be made to cargo inspection system 10 without departing from the scope of the invention. The components of cargo inspection system 10 may be integrated or separated. For example, customs offices 38 may be co-located with its associated secure terminal 34, or customs offices 38 may be located remotely from secure terminal 34 such that control over guideway vehicles 24 entering and leaving secure terminal 34 are provided by one or more additional communication links between customs office 38 and secure terminal 34. Moreover, the operations of cargo inspection system 10 may be performed by more, fewer, or other components. For example, cargo inspection system 10 may be configured with surveillance equipment, such as video cameras, configured along guideway 26 to determine if guideway vehicles 24 are tampered with during transit between first inspection station 12 and second inspection station 14.

Although the present disclosure has been described with several embodiments, a myriad of changes, variations, alterations, transformations, and modifications may be suggested to one skilled in the art, and it is intended that the present disclosure encompass such changes, variations, alterations, transformation, and modifications as they fall within the scope of the appended claims.

What is claimed is:

1. A cargo inspection method comprising:
transporting a first guideway vehicle over a guideway from a first inspection station to a second inspection station without stopping, the guideway spanning over a national boundary, the first inspection station being associated with a first government entity, the second inspection station being associated with a second government entity;
while moving the first guideway vehicle through the first inspection station, using a first non-intrusive scanning mechanism associated with the first inspection station to acquire a first set of data associated with cargo stored in the first guideway vehicle;
while the first guideway vehicle is in transit between the first inspection station and the second inspection station, analyzing the first set of data acquired by the first non-intrusive scanning mechanism associated with the first inspection station to determine the identity of the cargo stored on the first guideway vehicle;
comparing the first set of data acquired by the first non-intrusive scanning mechanism with a first manifest that describes the cargo that is declared to be stored on the first guideway vehicle;
in response to determining that the identity of the cargo does not match the first manifest, segregating the first guideway vehicle from the guideway and diverting the first guideway vehicle to a manual inspection depot for a manual inspection of the first guideway vehicle at the second inspection station.

2. A cargo inspection method comprising:
transporting a first guideway vehicle over a guideway from a first inspection station to a second inspection station without stopping, the second inspection station being remotely located from the first inspection station;
while moving the first guideway vehicle through the first inspection station, using a first non-intrusive scanning mechanism associated with the first inspection station to acquire a first set of data associated with cargo stored in the first guideway vehicle;
while the first guideway vehicle is in transmit between the first inspection station and the second inspection station, analyzing the first set of data acquired by the first non-intrusive scanning mechanism associated with the first inspection station to determine the identity of the cargo stored on the first guideway vehicle;
comparing the first set of data acquired by the first non-intrusive scanning mechanism with a first manifest that describes the cargo that is declared to be stored on the first guideway vehicle;
determining that the first guideway vehicle contains contraband cargo if the identity of the cargo does not match the first manifest; and
determining that the first guideway vehicle does not contain contraband cargo if the identity of the cargo matches the first manifest.

3. The cargo inspection method of claim 2, wherein using the non-intrusive scanning mechanism to acquire the first set of data comprises generating imagery of the cargo stored in the first guideway vehicle.

4. The cargo inspection method of claim 2, wherein:
the guideway extends over a national boundary;
the first inspection station is associated with a first customs agency associated with a first government entity; and
the second inspection station is associated with a second customs agency associated with a second government entity.

5. The cargo inspection method of claim 2, wherein the guideway vehicle is restricted from stopping while being transported over the guideway from the second inspection station to the first inspection station.

6. The cargo inspection method of claim 2, wherein the guideway vehicle is unmanned.

7. The cargo inspection method of claim 2, wherein the non-intrusive scanning mechanism is selected from the group consisting of an X-ray machine, a gamma ray detection machine, and a computing tomography (CT) scanning machine.

8. The cargo inspection method of claim 2, wherein using the first non-intrusive scanning mechanism comprises projecting energy toward the first guideway vehicle in a serial manner such that the energy is directed at the first guideway vehicle from a single direction.

9. The cargo inspection method of claim 2, wherein using the first non-intrusive scanning mechanism comprises projecting energy toward the first guideway vehicle in a multi-axial manner such that the energy is directed at the first guideway vehicle from a plurality of directions.

10. The cargo inspection method of claim 2, wherein using the first non-intrusive scanning mechanism comprises:
performing a plurality of scans of a plurality of individual slices of the first guideway vehicle; and
generating the first set of data by combining the data acquired from the plurality of scans of the plurality of individual slices of the first guideway vehicle.

11. The cargo inspection method of claim 2, wherein using the first non-intrusive scanning mechanism associated with the first inspection station comprises transporting the first guideway vehicle through one of a plurality of stalls associated with the first inspection station, the first guideway vehicle transported without stopping.

12. The cargo inspection method of claim 2, further comprising:
transporting a second guideway vehicle over the guideway from the second inspection station to the first inspection station;
using a second non-intrusive scanning mechanism associated with the second inspection station to acquire a second set of data associated with cargo stored in the second guideway vehicle;
analyzing the second set of data acquired by the second non-intrusive scanning mechanism associated with the second inspection station to determine the identity of the cargo stored on the second guideway vehicle;
comparing the second set of data acquired by the second non-intrusive scanning mechanism with a second manifest that describes the cargo that is declared to be stored on the second guideway vehicle;
determining that the second guideway vehicle contains contraband cargo if the identity of the cargo does not match the second manifest; and
determining that the second guideway vehicle does not contain contraband cargo if the identity of the cargo matches the second manifest.

13. A cargo inspection system comprising:
a first guideway vehicle storing a first load of cargo; and
a guideway configured for transporting the first guideway vehicle between a first inspection station and a second inspection station without stopping, the second inspection station remotely located from the first inspection station, and
wherein the first inspection station is operable to:
while the first guideway vehicle is moving through the first inspection station, use a first non-intrusive scanning mechanism to acquire a first set of data associated with cargo stored in the first guideway vehicle;
while the first guideway vehicle is in transmit between the first inspection station and the second inspection station, analyze the first set of data acquired by the first non-intrusive scanning mechanism associated with the first inspection station to determine the identity of the cargo stored on the first guideway vehicle; and
transmit the first set of data to the second inspection station;

wherein the second inspection station is operable to:
compare the first set of data acquired by the first non-intrusive scanning mechanism with a first manifest that describes the cargo that is declared to be stored on the first guideway vehicle; and
determine that the first guideway vehicle contains contraband cargo if the identity of the cargo does not match the first manifest; and
determine that the first guideway vehicle does not contain contraband cargo if the identity of the cargo matches the first manifest.

14. The cargo inspection system of claim 13, wherein the non-intrusive scanning mechanism is operable to acquire the first set of data by generating imagery of the cargo stored in the first guideway vehicle.

15. The cargo inspection system of claim 13, wherein:
the guideway extends over a national boundary;
the first inspection station is associated with a first customs agency associated with a first government entity; and
the second inspection station is associated with a second customs agency associated with a second government entity.

16. The cargo inspection system of claim 13, wherein the first guideway vehicle is restricted from stopping while being transported over the guideway from the second inspection station to the first inspection station.

17. The cargo inspection system of claim 13, wherein the guideway vehicle is unmanned.

18. The cargo inspection system of claim 13, wherein the first non-intrusive scanning mechanism is selected from the group consisting of an X-ray machine, a gamma ray detection machine, and a computing tomography (CT) scanning machine.

19. The cargo inspection system of claim 13, wherein the first non-intrusive scanning mechanism is operable to project energy toward the first guideway vehicle in a serial manner such that the energy is directed at the first guideway vehicle from a single direction.

20. The cargo inspection system of claim 13, wherein the first non-intrusive scanning mechanism is operable to project energy toward the first guideway vehicle in a multi-axial manner such that the energy is directed at the first guideway vehicle from a plurality of directions.

21. The cargo inspection system of claim 13, wherein the first non-intrusive scanning mechanism is operable to:
perform a plurality of scans of a plurality of individual slices of the first guideway vehicle; and
generate the first set of data by combining the data acquired from the plurality of scans of the plurality of individual slices of the first guideway vehicle.

22. The cargo inspection system of claim 13, wherein the first inspection station comprises a plurality of stalls, the first non-intrusive scanning mechanism operable to scan the first guideway vehicle as the first guideway vehicle is transported, without stopping, through a selected one of the plurality of stalls.

23. The cargo inspection system of claim 13, further comprising:
a second guideway vehicle storing a second load of cargo; and
wherein the second inspection station is operable to:
use a second non-intrusive scanning mechanism to acquire a second set of data associated with cargo stored in the second guideway vehicle;
analyze the second set of data acquired by the second non-intrusive scanning mechanism associated with the second inspection station to determine the identity of the cargo stored on the second guideway vehicle; and transmit the second set of data to the first inspection station;

wherein the first inspection station is operable to:

compare the second set of data acquired by the second non-intrusive scanning mechanism with a second manifest that describes the cargo that is declared to be stored on the second guideway vehicle; and determine that the second guideway vehicle contains contraband cargo if the identity of the cargo does not match the second manifest; and determine that the second guideway vehicle does not contain contraband cargo if the identity of the cargo matches the second manifest.

* * * * *